(12) United States Patent
Kakutani

(10) Patent No.: US 11,478,279 B2
(45) Date of Patent: Oct. 25, 2022

(54) SPINAL FUSION IMPLANT

(71) Applicant: NATIONAL UNIVERSITY CORPORATION KOBE UNIVERSITY, Hyogo (JP)

(72) Inventor: Kenichiro Kakutani, Kobe (JP)

(73) Assignee: NATIONAL UNIVERSITY CORPORATION KOBE UNIVERSITY, Hyogo (JP)

( * ) Notice: Subject to any disclaimer, the term of this patent is extended or adjusted under 35 U.S.C. 154(b) by 41 days.

(21) Appl. No.: 16/620,138

(22) PCT Filed: May 30, 2018

(86) PCT No.: PCT/JP2018/020636
§ 371 (c)(1),
(2) Date: Dec. 6, 2019

(87) PCT Pub. No.: WO2018/225588
PCT Pub. Date: Dec. 13, 2018

(65) Prior Publication Data
US 2020/0197047 A1 Jun. 25, 2020

(30) Foreign Application Priority Data

Jun. 8, 2017 (JP) .............................. JP2017-113495

(51) Int. Cl.
*A61B 17/70* (2006.01)

(52) U.S. Cl.
CPC ...... *A61B 17/7011* (2013.01); *A61B 17/7049* (2013.01)

(58) Field of Classification Search
CPC ............ A61B 17/7011; A61B 17/7049; A61B 17/7046; A61B 17/7043; A61B 17/80; A61B 17/7044; A61B 17/7059

(Continued)

(56) References Cited

U.S. PATENT DOCUMENTS 5,306,275 A * 4/1994 Bryan ................ A61B 17/1757
606/250
7,220,262 B1 * 5/2007 Hynes ................ A61B 17/7011
606/279

(Continued)

FOREIGN PATENT DOCUMENTS

JP  2006-523502 A  10/2006
KR  20150067809 A  6/2015
WO  WO-0164144 A2 *  9/2001  ......... A61B 17/7059

OTHER PUBLICATIONS

International Search Report issued in PCT/JP2018/020636 dated Jul. 24, 2018 (1 page).

(Continued)

*Primary Examiner* — Eduardo C Robert
*Assistant Examiner* — David C Comstock
(74) *Attorney, Agent, or Firm* — Osha Bergman Watanabe & Burton LLP

(57) ABSTRACT

The purpose of the present invention is to provide a spinal fusion implant capable of preserving turning properties of vertebral bodies, and in addition, capable of preventing false screwing (false insertion) of screws. Connection plates 3 constituting a spinal fusion implant 101 each have, on a ventral-side surface 3b, a convex-shaped portion 8 that is fitted into a concave-shaped portion of an intervertebral joint 53. In addition, a center hole 3d through which a center rod 4 is slidably inserted is formed on a side surface of the connection plate 3, such that the center of the hole is positioned closer to the back side than a virtual line L1 connecting midpoints on arc-shaped contour lines C of the concave-shaped portions of the adjacent intervertebral joints 53 when viewed from the head side of a human body.

10 Claims, 12 Drawing Sheets

(58) Field of Classification Search
USPC .................... 606/264, 265, 272, 277, 278
See application file for complete search history.

(56) References Cited

U.S. PATENT DOCUMENTS

| | | | | |
|---|---|---|---|---|
| 8,308,768 B2* | 11/2012 | Fauth | ................ | A61B 17/7067 606/247 |
| 9,283,001 B2* | 3/2016 | Harper | ............... | A61B 17/7049 |
| 9,717,541 B2* | 8/2017 | Lee et al. | ........... | A61B 17/7059 606/86 A |
| 9,763,705 B2* | 9/2017 | Faulhaber | .......... | A61B 17/7032 |
| 10,842,539 B2* | 11/2020 | Faulhaber | .......... | A61B 17/1757 606/96 |
| 2002/0019633 A1* | 2/2002 | Ray | .................. | A61B 17/7044 606/53 |
| 2004/0210216 A1 | 10/2004 | Farris et al. | | |
| 2005/0033434 A1* | 2/2005 | Berry | ................ | A61B 17/7064 623/17.14 |
| 2005/0288669 A1* | 12/2005 | Abdou | ............... | A61B 17/7055 606/246 |
| 2007/0185489 A1* | 8/2007 | Abdou | ................. | A61F 2/4425 606/255 |
| 2008/0021454 A1* | 1/2008 | Chao et al. | ........ | A61B 17/8009 606/282 |
| 2008/0109039 A1* | 5/2008 | Michielli | ........... | A61B 17/7059 606/264 |
| 2009/0318968 A1 | 12/2009 | Duggal et al. | | |
| 2010/0082067 A1 | 4/2010 | Kondrashov | | |
| 2011/0160771 A1* | 6/2011 | Wang | ................ | A61B 17/7059 606/246 |
| 2015/0088206 A1* | 3/2015 | Bullard | ............. | A61B 17/8057 606/246 |
| 2016/0151095 A1* | 6/2016 | Harper | ............... | A61B 17/7049 606/279 |
| 2016/0270924 A1* | 9/2016 | Faulhaber | ........... | A61B 17/8047 |

OTHER PUBLICATIONS

Written Opinion of the International Searching Authority issued in in PCT/JP2018/020636 dated Jul. 24, 2018 (4 pages).
Extended European Search Report issued in counterpart European Patent Application No. 18814248.3, dated Feb. 24, 2021 (11 pages).
Office Action in counterpart Japanese Patent Application No. 2019-523475 dated Jun. 28, 2022 (12 pages).

* cited by examiner

SPINAL FUSION IMPLANT

TECHNICAL FIELD

The present invention relates to a spinal fusion implant which keeps the relative positions of neighboring vertebral bodies to fall within a predetermined range.

BACKGROUND ART

An example of this technology is recited in Patent Literature 1. A spinal fusion system recited in Patent Literature 1 includes screws fixed to vertebral bodies, which are regarded as fixing members, and rods connecting the screws with each other. As shown in, for example, FIG. 5 of Patent Literature 1, two screws are screwed (punctured) into and fixed to a vertebral body in each vertebra. The relative positions of neighboring vertebral bodies are fixed by two groups of screws and rods, which are arranged to be in parallel. The document further recites that, in order to further firmly fix the vertebral bodies with each other, the neighboring rods may be connected to each other by a lateral connector.

Although not clearly recited in Patent Literature 1, the screws, the rods, and the lateral connector are made of a metal material such as titanium.

CITATION LIST

Patent Literatures

[Patent Literature 1] Published Japanese Translation of a PCT application No. 2006-523502 (Tokuhyo 2006-523502)

SUMMARY OF INVENTION

Technical Problem

The known spinal fusion implant recited in Patent Literature 1 completely fixes the neighboring vertebral bodies to each other. Because the relative positions of the completely fixed vertebral bodies do not change at all, the rotation range of the waist of the patient is narrowed after the surgery, and it becomes difficult to rotate the waist. The daily life of the patient may therefore be affected after the surgery. Furthermore, a bone fracture may occur between the completely fixed vertebral body and a neighboring vertebral body which is not fixed. The rotational angle of five lumbar vertebrae (vertebrae) is typically about 10 degrees, and hence the rotational angle per each vertebral body is about 2 degrees.

In addition to the above, the known spinal fusion implant recited in Patent Literature 1 involves the following problem. When an operator screws a screw into a vertebral body, erroneous screwing (erroneous puncture) occurs at a non-negligible rate (about 5 to 10%). In this regard, a spinal cord extends in a spinal canal which is between a vertebral body and a vertebral arch constituting a vertebra. The heart, various organs, the aorta, the vena cava, etc. are on the belly side of the vertebral bodies. When, for example, the spinal cord is damaged by erroneous screwing (erroneous puncture) of a screw, neuralgia or paralytic symptoms may occur. Furthermore, massive hemorrhage may occur when a large vessel such as the aorta is damaged.

In order to prevent the occurrence of erroneous screwing (erroneous puncture) of a screw into a vertebral body, some hospitals have three-dimensional monitoring systems (navigation systems) which are very expensive. However, not all hospitals are able to have such systems for various reasons.

The present invention has been done under the circumference described above, and an object of the present invention is to provide a spinal fusion implant by which the rotatability of vertebral bodies is less hindered and erroneous screwing (erroneous puncture) of a screw is prevented.

Solution to Problem

A spinal fusion implant provided by the present invention, which keeps relative positions of neighboring vertebral bodies to fall within a predetermined range, includes: screws connected to vertebral bodies; at least two connection plates in each of which guide holes into which the screws are inserted from a back side surface toward a belly side surface are formed at both end portions; and a center rod which connects neighboring ones of the connection plates which are fixed to the vertebral bodies by the screws. Each of the connection plates has, on the belly side surface, protrusions which are fitted into concave portions of intervertebral joints, and a center hole into which the center rod is slidably inserted is formed in side surfaces of each of the connection plates so that the center of the center hole is on the back side of an imaginary line which connects middle points of arc-shaped contour lines of the concave portions of the neighboring intervertebral joints when viewed from the head side of a human body.

As described in The Physiology of the Joints written by I. A. Kapandji, which is renowned in the field of orthopedics, the assumed rotation center of a vertebral body is positioned at the center of an imaginary circle assumed from arc-shaped contour lines of the concave portions of the intervertebral joints when viewed from the head side of the human body. The center of the center hole into which the center rod is slidably inserted may not be identical with the assumed rotation center of the vertebral body, but the assumed rotation center of the vertebral body is on the back side of the vertebral body. The vertebral body is therefore rotatable about the center rod together with the connection plate, and hence the rotation of the vertebral body is less hindered.

In addition to the above, the connection plate has, on the belly side surface, the protrusions which are fitted into the concave portions of the intervertebral joints. This arrangement allows the connection plate to be closely in contact with the back side of the vertebra. This minimizes the rattling and deviation of the screw in screwing (puncture). Furthermore, as the protrusions of the connection plate are fitted into the concave portions of the intervertebral joints, the screwing positions and angles of the screws are correctly determined. As a result, the occurrence of erroneous screwing (erroneous puncture) is prevented as compared to conventional ones. Furthermore, because the belly side surface of the connection plate contributes to the integration of the vertebra and the connection plate, bone fracture of the vertebra is prevented while the rotatability of the vertebra is less hindered.

According to a preferred embodiment of the present invention, the center hole is positioned at the center of an imaginary circle which is assumed from the contour lines.

This arrangement further facilitates the rotatability of the vertebral bodies.

According to a preferred embodiment of the present invention, the center rod is curved based on data of a row of vertebrae in an upright position.

This arrangement further facilitates the rotatability of the vertebral bodies when the patient is in an upright position, in particular when the patient is in action after the surgery.

According to a preferred embodiment of the present invention, the center rod is curved along an imaginary curve which is formed by connecting centers of imaginary circles assumed from the contour lines, in a direction in which the vertebrae are lined up.

This arrangement further facilitates the rotatability of the vertebral bodies.

According to a preferred embodiment of the present invention, positions and angles of the guide holes in each of the connection plates are determined for each of the vertebral bodies so that the screws are accommodated inside the vertebral bodies.

This arrangement prevents the spinal cord, the heart, the organs, or large vessels such as the aorta from being damaged by the screws, and the screws are screwed (punctured) more safely.

According to a preferred embodiment of the present invention, the center rod is made of a resin material or a carbon fiber material.

The resin material and the carbon fiber material have a certain degree of flexibility. For this reason, in addition to a lesser degree of hindrance to the rotatability of the vertebral bodies, the flexibility (front/back flexibility) of the vertebral bodies is less hindered.

According to a preferred embodiment of the present invention, the screws, the connection plates, and the center rod are made of a resin material or a carbon fiber material.

With this arrangement, in addition to a lesser degree of hindrance to the rotatability and flexibility of the vertebral bodies, the occurrence of an artifact which is a problem for metal implants is prevented.

According to a preferred embodiment of the present invention, the spinal fusion implant further includes a lateral rod which is provided on either side of the center rod to connect neighboring ones of the connection plates, the lateral rod being made of a resin material or a carbon fiber material.

With this arrangement, in addition to a lesser degree of hindrance to the rotatability of the vertebral bodies, the vertebral bodies are firmly fixed to one another.

According to a preferred embodiment of the present invention, the number of the connection plates is three or more and the connection plates are lined up in series, and at least two of the connection plates are further connected with one another by lateral rods which are provided on the respective sides of the center rod.

With this arrangement, a part where the rotatability of the vertebral bodies is preferred and a part where the fixation of the vertebral bodies is preferred can coexist.

Advantageous Effects of Invention

The present invention is able to provide a spinal fusion implant by which the rotatability of vertebral bodies is less hindered and erroneous screwing (erroneous puncture) of a screw is prevented.

DESCRIPTION OF EMBODIMENTS

Figure 1:
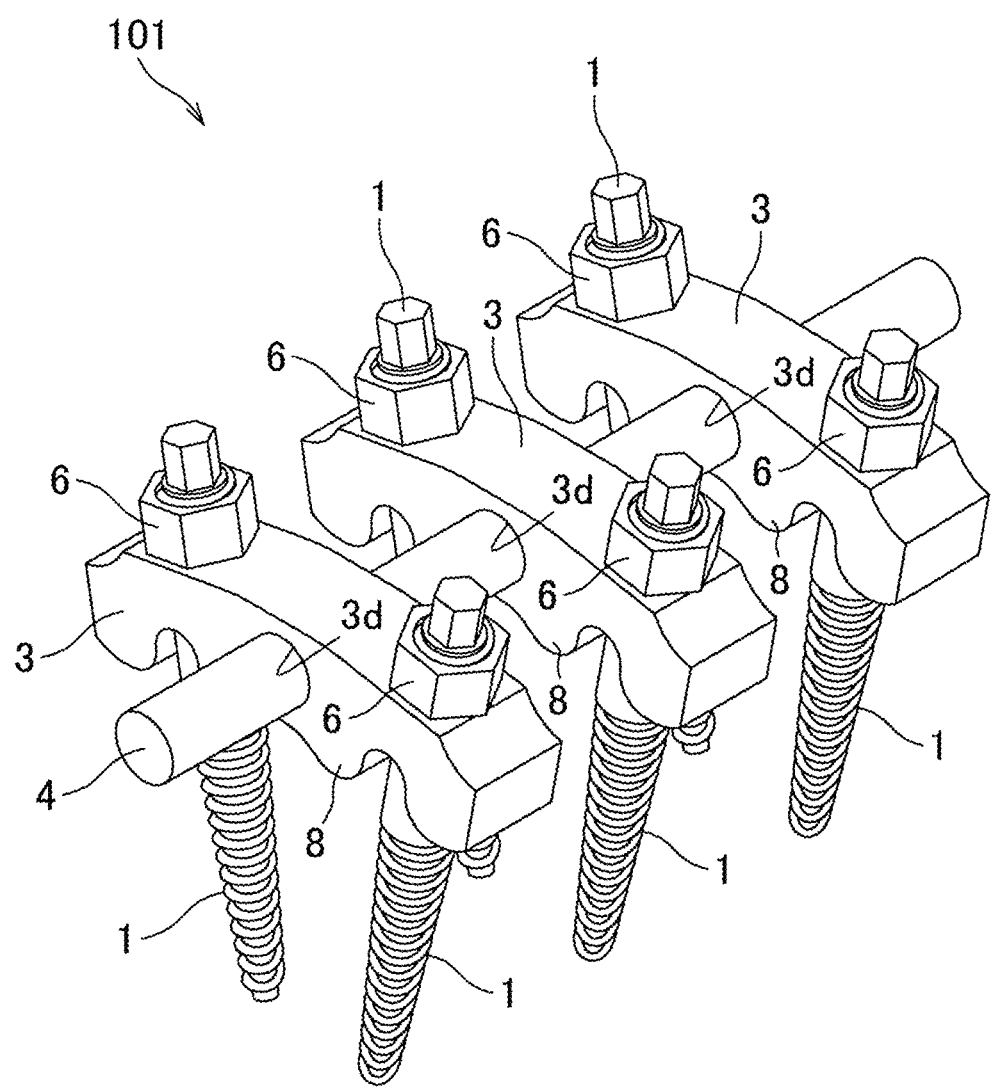
FIG. 1 is a perspective view of a spinal fusion implant of First Embodiment of the present invention.

The following will describe an embodiment of the present invention with reference to figures.

(Structure of Spinal Fusion Implant)

The structure of a spinal fusion implant 101 of First Embodiment of the present invention will be described with reference to FIG. 1 to FIG. 5. The spinal fusion implant 101 is an implant which keeps the relative positions of neighboring vertebral bodies 51 to fall within a predetermined range, and main components of this spinal fusion implant 101 are plural screws 1 fixed to the vertebral bodies 51, at least two connection plates 3, and a center rod 4 connecting the neighboring connection plates 3 with each other.

The phrase "keeping the relative positions of neighboring vertebral bodies 51 to fall within a predetermined range" indicates that the implant of the present invention does not completely fix vertebral bodies as in the case of the known spinal fusion implant, and is a spinal fusion implant with which the movability of the vertebral bodies is less hindered.

<Screw>

The screw 1 is a member by which the connection plate 3 is fixed to a vertebral body 51, and includes a tapered screw part 1$a$, a cylindrical part 1$b$, a parallel screw part 1$c$, and a hexagonal prism part 1$d$, which are provided in this order from the leading end side. The screw 1 is made of resin (plastic), carbon fibers, metal, or a composite of these materials. (The same applies to the connection plates 3, the center rod 4, and later-described lateral rods 5.) Examples of the resin material include PEEK resin (polyether ether ketone resin) and PLA resin (polylactic resin). Examples of the metal material include titanium, titanium alloy, cobalt chromium alloy, and stainless steel.

<Connection Plate>

The connection plates 3 are members fixed to the vertebral bodies 51 by the screws 1 and connect the vertebral bodies 51 which are adjacent to each other by means of the center rod 4. At the both end portions of the connection plate 3, guide holes 3$c$ are formed to allow the screws 1 to be inserted from a back side surface 3a to a belly side surface 3b opposite to the back side surface 3a.

Furthermore, the connection plate 3 has, on the belly side surface 3b, protrusions 8 which are fitted into concave portions of intervertebral joints 53. A vertebra 50 is formed of components such as a vertebral body 51, a vertebral arch 52, intervertebral joints 53, transverse processes 54, pedicles 55, and a spinous process. The spinous process has been removed from the vertebra 50 shown in FIG. 2. The spinous process and the vertebral arch 52 have been removed from the vertebra 50 shown in FIG. 4. Before screwing the screw 1 into the vertebral body 51, the operator causes the protrusions 8 of the connection plate 3 to fit into the concave portions of the intervertebral joints 53. As a result of this, the connection plate 3 is closely in contact with the back side of the vertebra 50. This minimizes the rattling and deviation of the screw 1 in the subsequent screwing (puncture). The positions and sizes of the protrusions 8 on the belly side surface 3b are preferably determined for each vertebra 50. For example, before the surgery, the shape and size of each vertebra 50 is measured in three dimensions by CT or MRI, and the positions and sizes of the protrusions 8 on the belly side surface 3b are determined in accordance with the concave portions of the intervertebral joints 53, in accordance with the measurement result. Then the connection plate 3 is manufactured for each vertebra 50.

Figure 2:
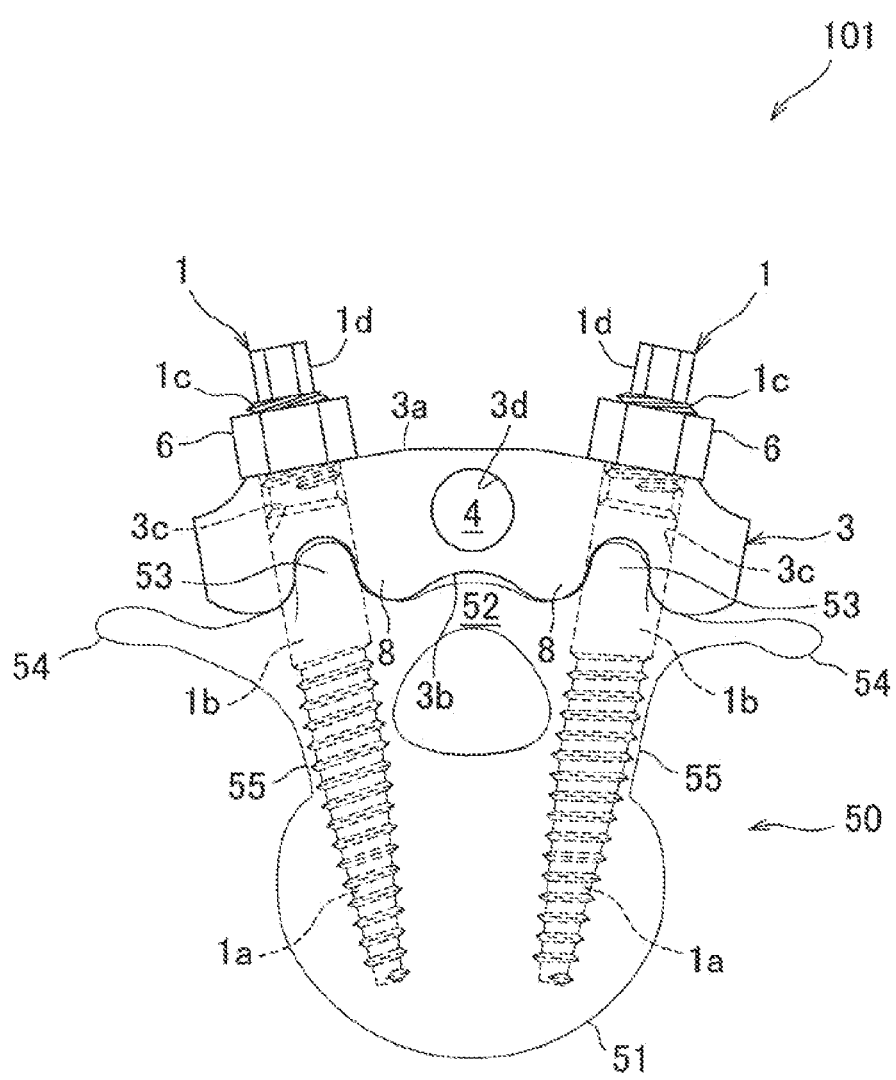
FIG. 2 is a front view of the spinal fusion implant shown in FIG. 1, and shows a vertebra together with the spinal fusion implant.
Figure 3:
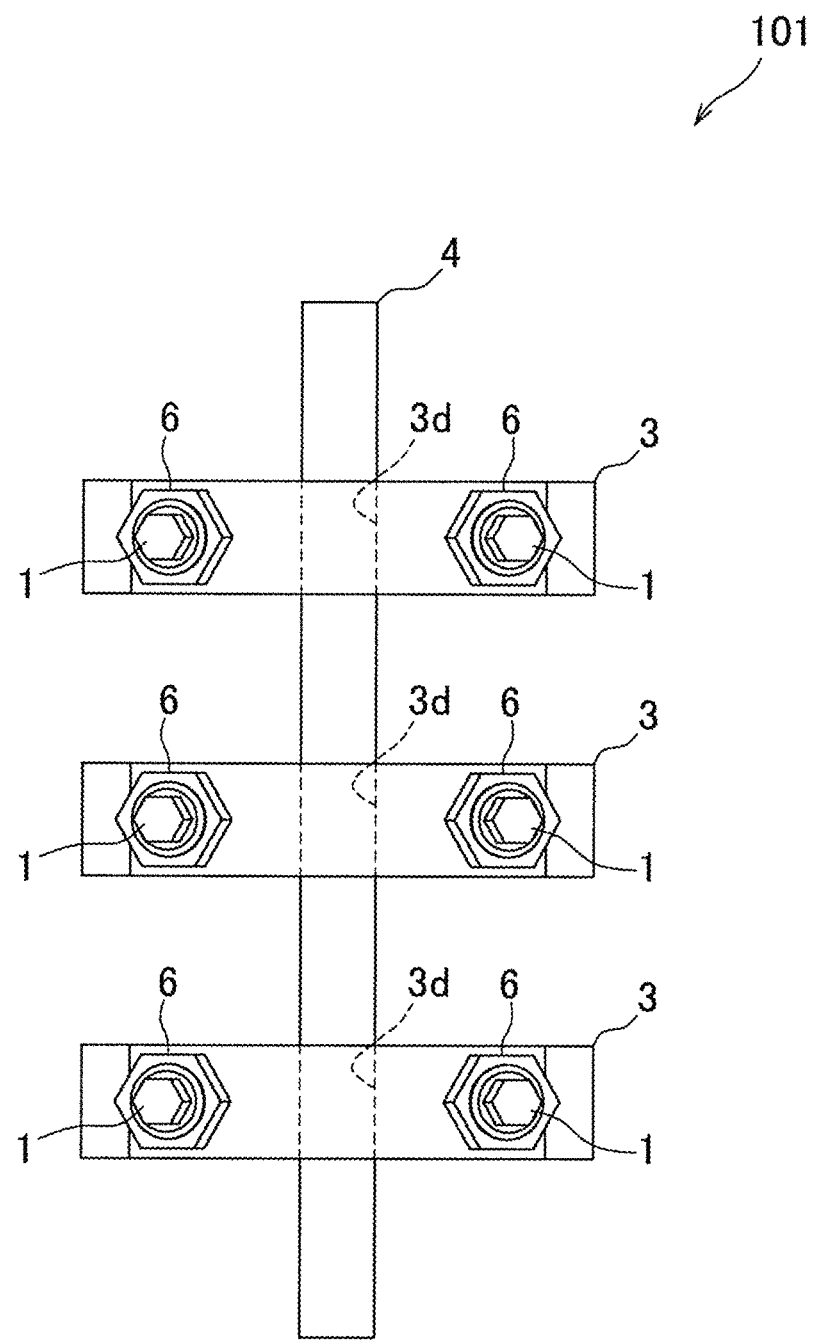
FIG. 3 is a front view of the spinal fusion implant shown in FIG. 1 (the vertebrae are not shown).

The positions and angles of the guide holes 3c in the connection plate 3 are preferably determined for each vertebral body 51 so that each tapered screw part 1a (screw 1) is accommodated inside the vertebral body 51 (see FIG. 2). As described above, for example, before the surgery, the shape and size of each vertebra 50 is measured in three dimensions by CT or MRI, and the positions and angles of the guide holes 3c in the connection plate 3 are determined to be optimal for each vertebral body so that each tapered screw part 1a (screw 1) is accommodated inside the vertebral body 51, in accordance with the measurement result. This prevents the spinal cord, the heart, the organs, or large vessels such as the aorta from being damaged by the screws 1, and the screws 1 are screwed (punctured) more safely.

A center hole 3d is formed in the side surfaces of the connection plate 3. The center rod 4 is slidably inserted into this center hole 3d. The connection plates 3 and the center rod 4 are not completely fixed, and the connection plates 3 are rotatable about the center rod 4.

Figure 4:
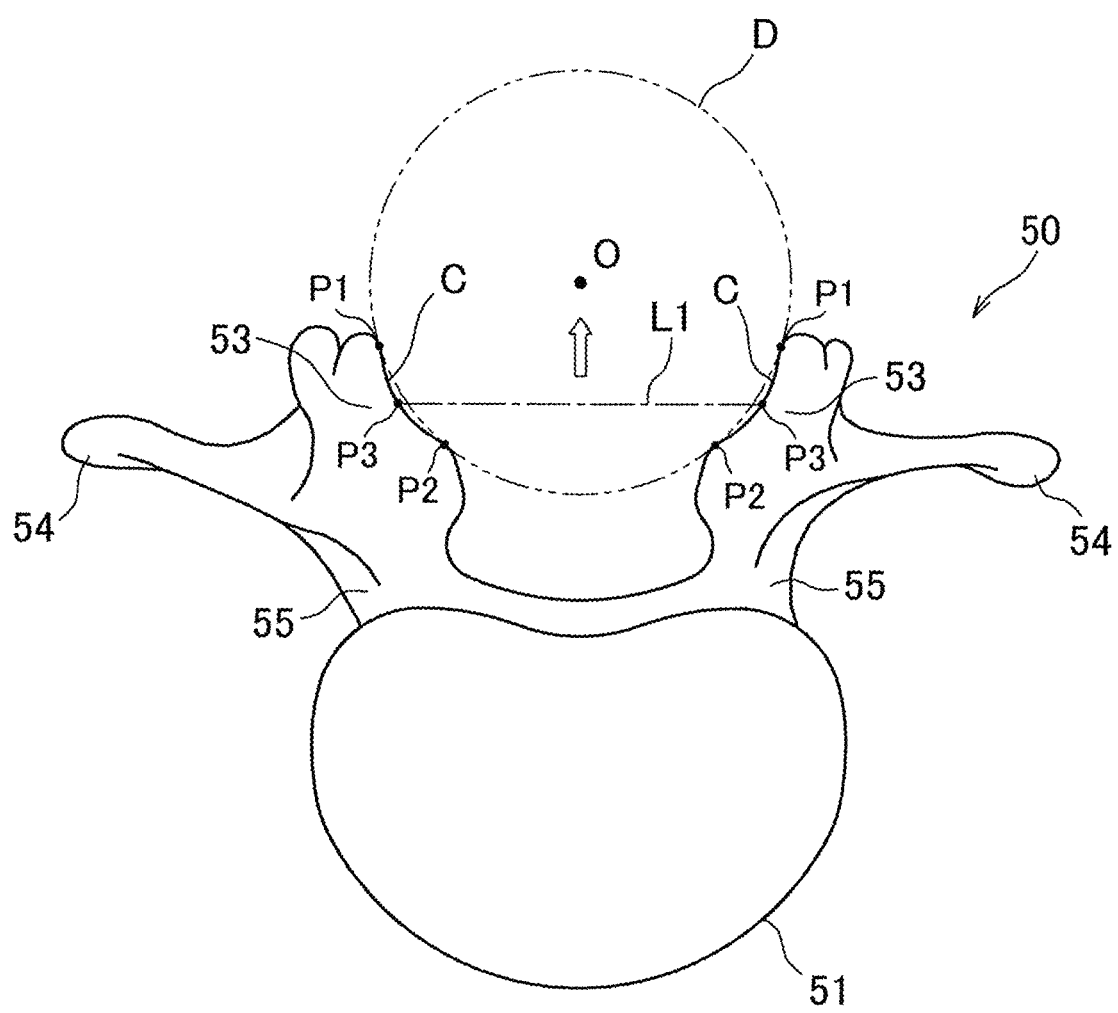
FIG. 4 is provided for explaining the assumed rotation center of a vertebral body, and shows a state in which a vertebra (lumbar vertebra) from which the spinous process and the vertebral arch are removed is viewed from the head side of the human body.

Now, the following will describe the assumed rotation center of the vertebral body 51 to which the connection plate 3 is fixed, with reference to FIG. 4. As described in The Physiology of the Joints above, it has been known that the assumed rotation center of a vertebral body 51 is the center O of an imaginary circle D shown in FIG. 4.

This imaginary circle D is a circle assumed such that arc-shaped contour lines C of the concave portions of the intervertebral joints 53 substantially form parts of the circumference, when viewed from the head side of the human body. The contour line C of each intervertebral joint 53 is scarcely a mathematically complete arc. On this account, the arc-shaped contour line C substantially forms a part of the circumference and may not be completely matched with the circumference of the imaginary circle D.

In order to arrange the rotatability of the vertebral body 51 to be less hindered, the center of the center hole 3d into which the center rod 4 is inserted is formed in the side surfaces of the connection plate 3 so that, in a state in which the connection plate 3 is fixed to the vertebral body 51, the center of the center hole 3d is on the back side of an imaginary line L1 which connects the middle points of the contour lines C of the neighboring intervertebral joints 53 when viewed from the head side of the human body. The middle point of the arc-shaped contour line C is a point P3 which is on the arc-shaped contour line C and is equally distanced from the both ends P1 and P2 of the contour line C.

The above-described center of the hole may not be identical with the assumed rotation center (i.e., the center O of the imaginary circle D) of the vertebral body 51, but is on the back side of the vertebral body for which the center O of the imaginary circle D is assumed. The vertebral body 51 is therefore rotatable about the center rod 4 together with the connection plate 3, and hence the rotatability of the vertebral body 51 is less hindered. As described above, the rotational angle of each vertebra constituting the lumbar vertebrae is small, i.e., about 2 degrees. For this reason, even if the center of the center hole 3d is not completely identical with the center O of the imaginary circle D, the vertebral body 51 is rotatable and hence the rotatability of the vertebral body 51 is less hindered.

The rotatability of the vertebral body 51 is further facilitated when, in a state that the connection plate 3 is fixed to the vertebral body 51, the center hole 3d into which the center rod 4 is inserted is formed in the side surfaces of the connection plate 3 so that the center hole 3d is positioned at the center O of the imaginary circle D, which is the assumed rotation center of the vertebral body 51 (i.e., the center of the center hole 3d is identical with the center O of the imaginary circle D).

Before the surgery, the shapes and sizes of the intervertebral joints 53 of each vertebra 50 are measured in three dimensions by CT or MRI, and the assumed rotation center of each vertebral body 51 is determined based on the measurement result. In the state that the connection plate 3 is fixed to the vertebral body 51, the center hole 3d is formed in the side surfaces of the connection plate 3 so that the center hole 3d is positioned at the determined rotation center.

<Center Rod>

The center rod 4 is a member for connecting neighboring connection plates 3 which are fixed to the vertebral bodies 51 by the screws 1.

In order to further facilitate the rotatability of the vertebral bodies 51, the center rod 4 is preferably curved based on the data of the row of vertebrae 50 in an upright position. The data of the row of vertebrae 50 in the upright position is acquired by, for example, radiography.

Figure 5:
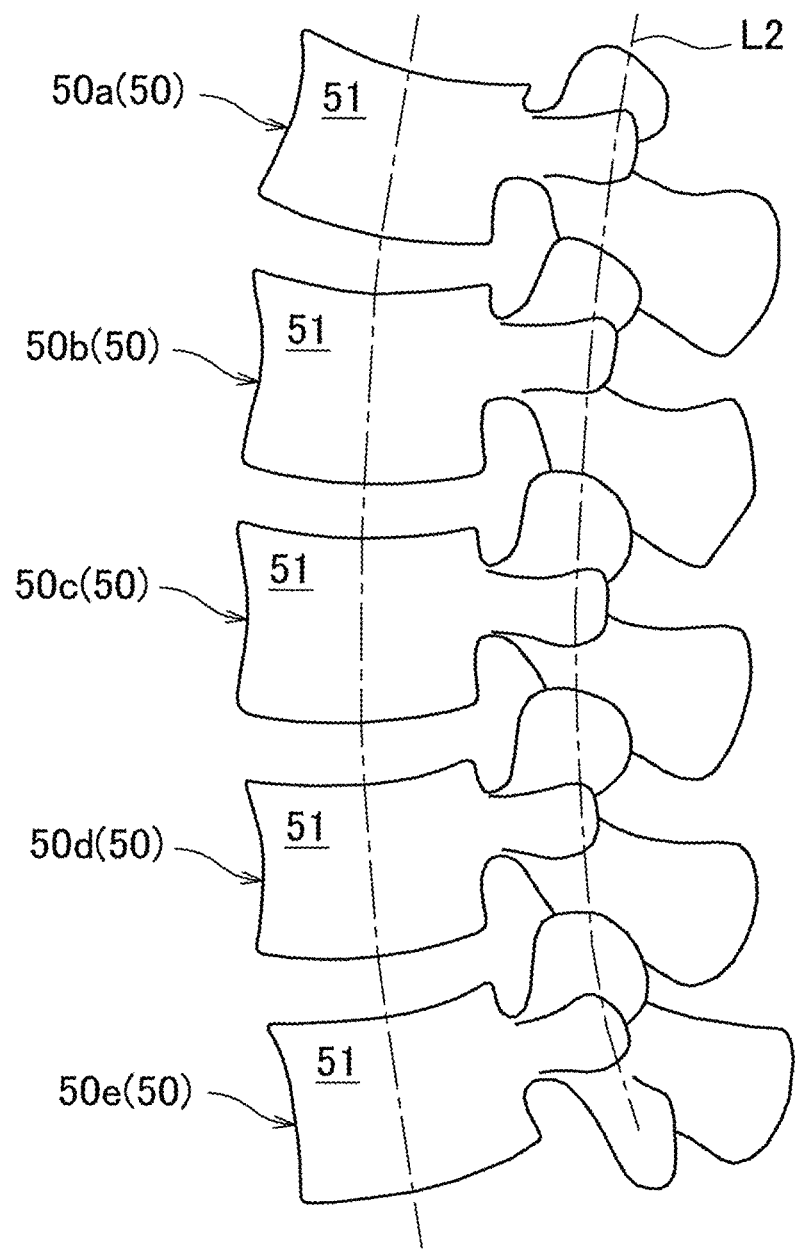
FIG. 5 is a side view of the five lumbar vertebrae constituting the spinal column in an upright position.

FIG. 5 is a side view of the five vertebrae 50 (lumbar vertebrae 50a to 50e) constituting the spinal column in the upright position. An imaginary curve L2 shown in FIG. 5 connects the centers O of the imaginary circles D shown in FIG. 4, in the direction in which the vertebrae 50 are lined up. In other words, the imaginary curve L2 connects the assumed rotation centers of the vertebral bodies 51, in the direction in which the vertebrae 50 are lined up. The center rod 4 is preferably curved along this imaginary curve L2. The depicted imaginary curve L2 penetrates the spinous processes. The spinous processes are removed in the surgery in order to allow the connection plates 3 to be fitted with the intervertebral joints 53.

As described above, before the surgery, the shapes and sizes of the intervertebral joints 53 of each vertebra 50 are measured in three dimensions by CT or MRI, and the assumed rotation center of each vertebral body 51 is determined based on the measurement result. The imaginary curve L2 connects the assumed rotation centers of the vertebral bodies 51, in the direction in which the vertebrae 50 are lined up.

In regard to the material, the center rod 4 is preferably made of a material with a certain degree of flexibility, e.g., resin (plastic) such as PEEK resin and carbon fibers. With this arrangement, in addition to a lesser degree of hindrance to the rotatability of the vertebral bodies 51, the flexibility (front/back flexibility) of the vertebral bodies 51 is less hindered.

(Method of Using Spinal Fusion Implant)

The following will describe how the spinal fusion implant 101 is used. To begin with, an operator cuts the back of the human body for a predetermined length so that the vertebrae 50 are exposed. Then the spinous processes are removed from implant-mounted part of the vertebrae 50. The vertebral arch 52 is typically not removed, but may be removed from the vertebra 50 according to need.

Subsequently, the connection plate 3 is closely attached to the back side of the vertebra 50 as the protrusions 8 of the connection plate 3 are fitted into the concave portions of the intervertebral joints 53. Then the screws 1 are inserted into the guide holes 3c of the connection plate 3, and the screws 1 are screwed (punctured) into the vertebral body 51. The operator puts a lug wrench on the hexagonal prism part 1d at the rear end portion of the screw 1, and screws (punctures) the screw 1 into the vertebral body 51 along the guide hole 3c, by slowly rotating the lug wrench.

After the screwing of the screw 1 is completed, a nut 6 is threaded onto the parallel screw part 1c of the screw 1 from the back side, so that the connection plate 3 is fixed to the vertebra 50. Subsequently, the center rod 4 is inserted into the center holes 3d of the neighboring connection plates 3, so that the connection plates 3 are connected to one another.

The center rod 4 is not fixed to the connection plates 3. The center rod 4, however, hardly drops off from the connection plates 3 on account of the spinous processes, etc. which are on the front and back of the center rod 4 in the axial direction.

Second Embodiment

Figure 6:
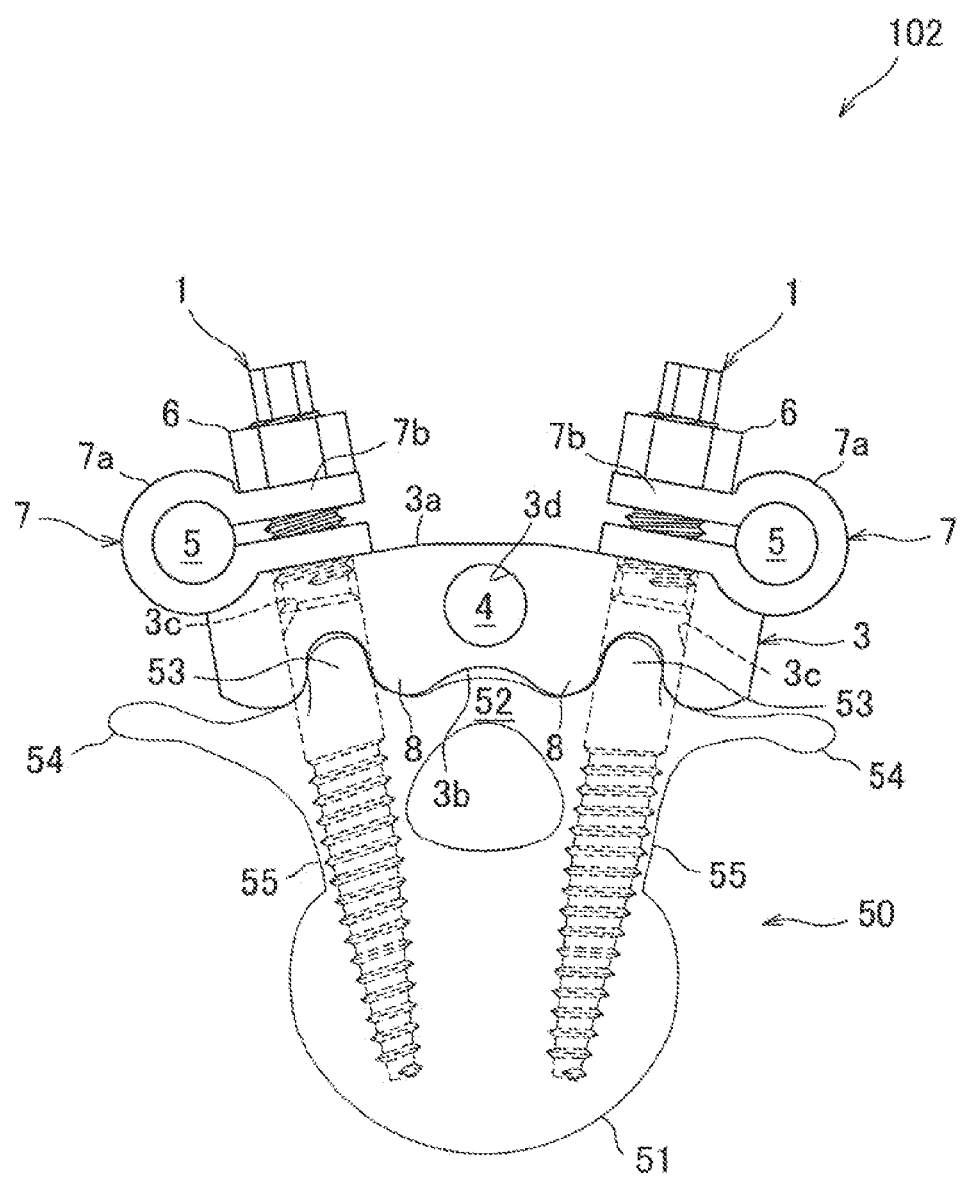
FIG. 6 is a front view of a spinal fusion implant of Second Embodiment of the present invention, and shows a vertebra together with the spinal fusion implant.
Figure 7:
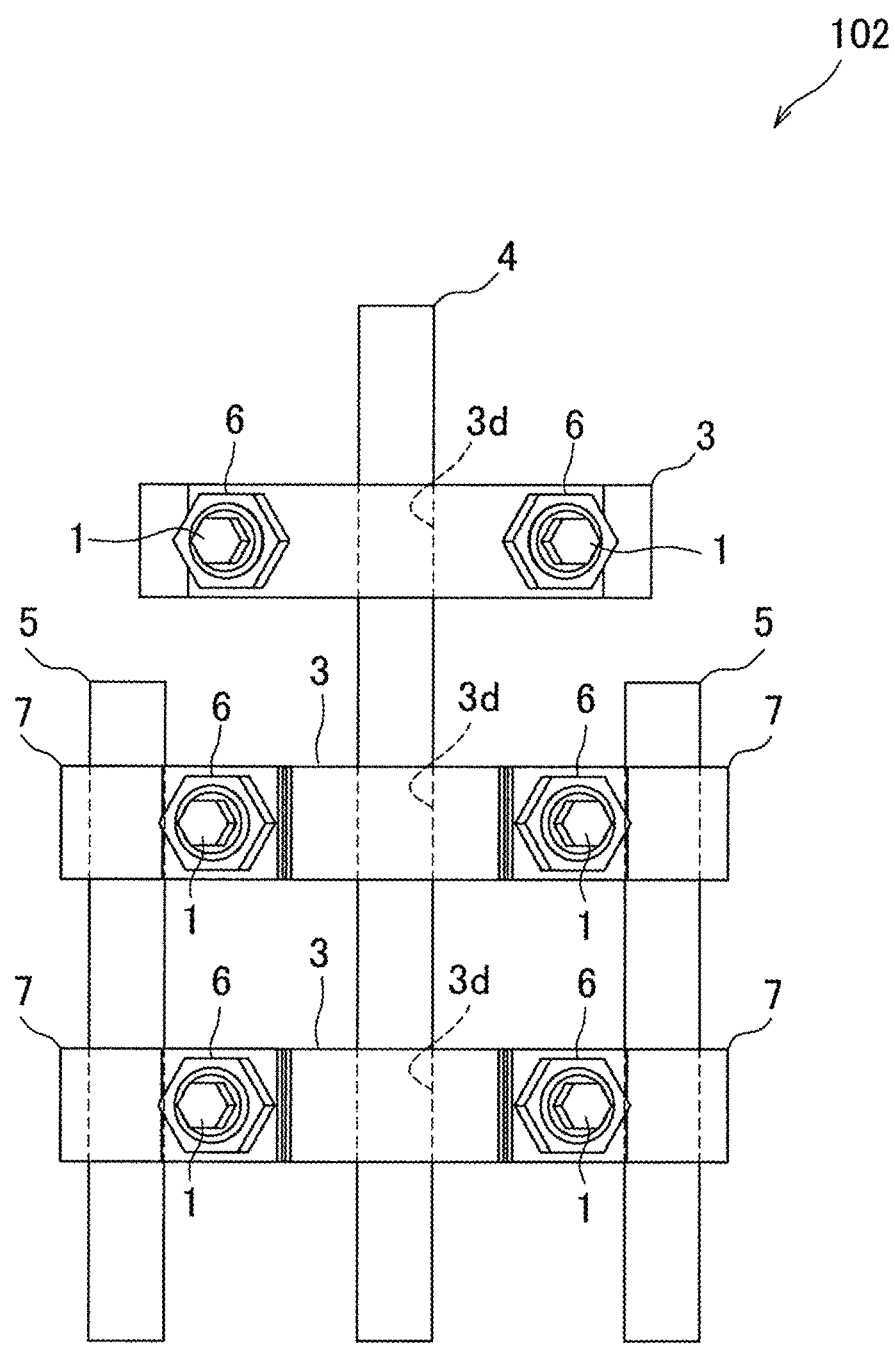
FIG. 7 is a front view of the spinal fusion implant shown in FIG. 6 (the vertebrae are not shown).

The structure of a spinal fusion implant 102 of Second Embodiment of the present invention will be described with reference to FIG. 6 and FIG. 7. In the spinal fusion implant 102 of Second Embodiment, members identical with those of the spinal fusion implant 101 of First Embodiment are denoted by the same reference symbols. (The same applies to later-described Third Embodiment.)

The spinal fusion implant 102 of Second Embodiment is different from the spinal fusion implant 101 of First Embodiment in that, in the spinal fusion implant 102 of Second Embodiment, some of the connection plates are connected with one another by lateral rods 5, in addition to the center rod 4.

The spinal fusion implant 102 includes three connection plates 3 provided in series, and two of these connection plates 3 are further connected with each other by lateral rods 5 which are provided on the respective sides of the center rod 4.

At the connection plates where the lateral rods 5 are provided, preference is given to the fixation of the vertebral bodies 51. Meanwhile, at the connection plate where the lateral rods 5 are not provided, preference is given to the rotatability of the vertebral bodies 51. In this way, the force of fixing the vertebral bodies 51 is partially enhanced by connecting some connection plates with one another by the lateral rods 5, in addition to the center rod 4. As such, the force of fixing each vertebral body 51 is changed depending on whether to use the lateral rods 5. A part where the rotatability of the vertebral bodies 51 is preferred and a part where the fixation of the vertebral bodies 51 is preferred can therefore coexist.

In the present embodiment, the lateral rods 5 are provided at the respective end portions of the connection plates 3, and the lateral rods 5 are attached to the connection plates 3 by using pin members 7. Each pin member 7 is composed of a ring-shaped rod holding portion 7a into which the lateral rod 5 is inserted and a leg portion 7b into which the screw 1 is inserted. In a state in which the lateral rod 5 is inserted into the rod holding portion 7a and the screw 1 is inserted into the leg portion 7b, a nut 6 is tightened from the back side. As a result, the leg portion 7b is elastically deformed and the lateral rod 5 is gripped by the rod holding portion 7a.

Alternatively, being similar to the attachment of the center rod 4 to the connection plate 3, the connection plate 3 may be connected to the lateral rods 5 in such a way that holes are bored in the side surfaces of the both end portions of the connection plate 3 and the lateral rods 5 are inserted into these holes. The connection plates 3 may or may not be fixed to the lateral rods 5. (The same applies to later-described Third Embodiment.)

Third Embodiment

Figure 8:
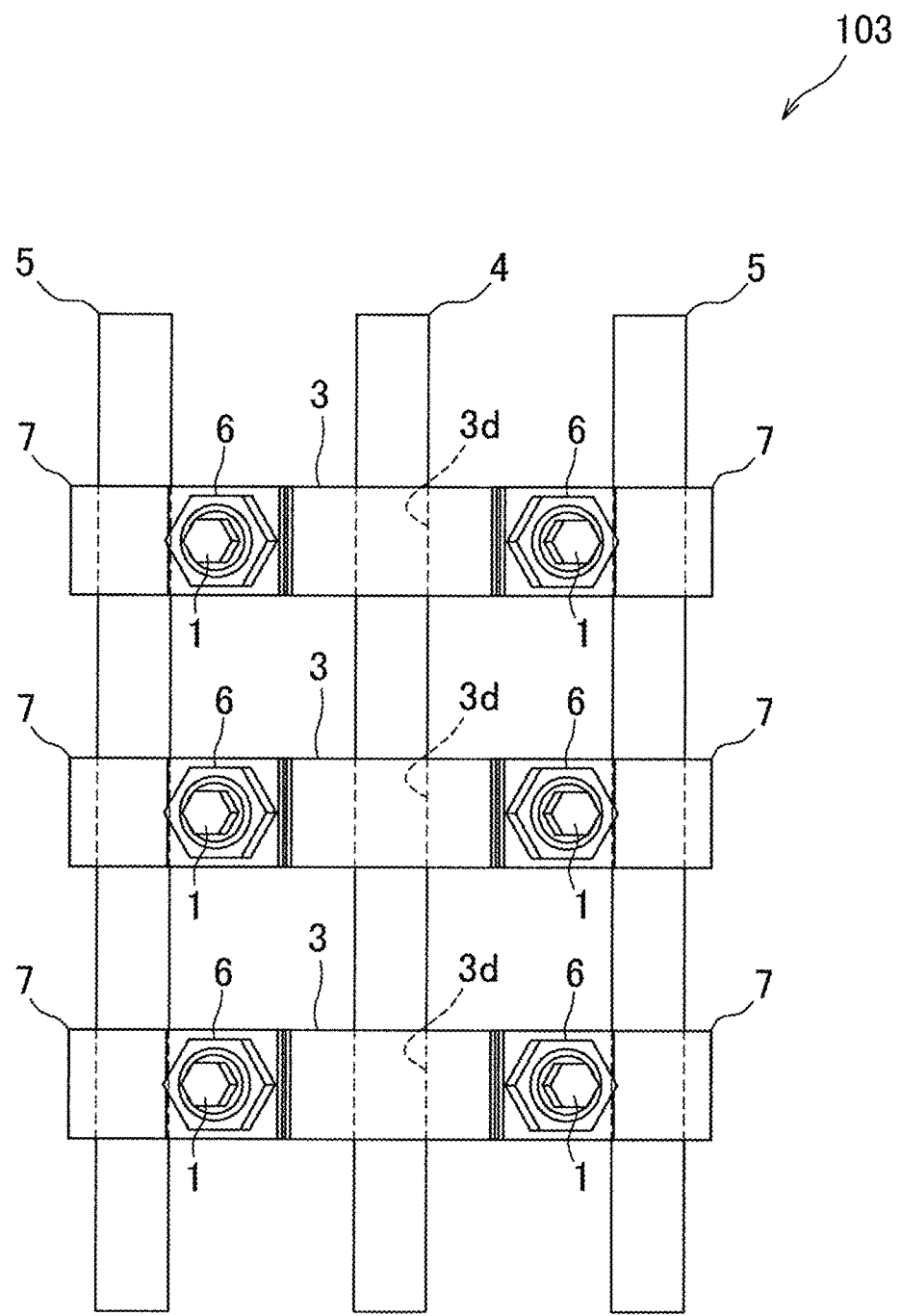
FIG. 8 is a plan view of a spinal fusion implant of Third Embodiment of the present invention (no vertebrae are shown).

The structure of a spinal fusion implant 103 of Third Embodiment of the present invention will be described with reference to FIG. 8 and FIG. 9.

The spinal fusion implant 103 of Third Embodiment is different from the spinal fusion implant 102 of Second Embodiment in that, in the spinal fusion implant 103 of Third Embodiment, all of the connection plates are connected with one another by lateral rods 5 which are provided on the respective sides of the center rod 4.

In this arrangement, in order to maintain the rotatability of the vertebral bodies 51, at least the connection plates 3, the center rod 4, and the lateral rods 5 are made of a material with a certain degree of flexibility, e.g., resin (plastic) such as PEEK resin and carbon fibers. The spinal fusion implant 103 of the present embodiment is slightly inferior to the spinal fusion implant 101 shown in FIG. 1, etc. having no lateral rods 5, in terms of the rotatability of the vertebral bodies 51. However, because the main components are made of a resin material or a carbon fiber material, the rotatability of the vertebral bodies 51 is less hindered in the spinal fusion implant 103 of the present embodiment, too.

In the spinal fusion implant 103 of the present embodiment, because two screws 1, a connection plate 3, and three rods (a center rod 4 and lateral rods 5) form a sort of frame structure, the vertebral bodies 51 are firmly fixed while the rotatability of the vertebral bodies 51 is less hindered. Furthermore, on account of the frame structure, a load on each component of the implant is distributed.

Figure 9:
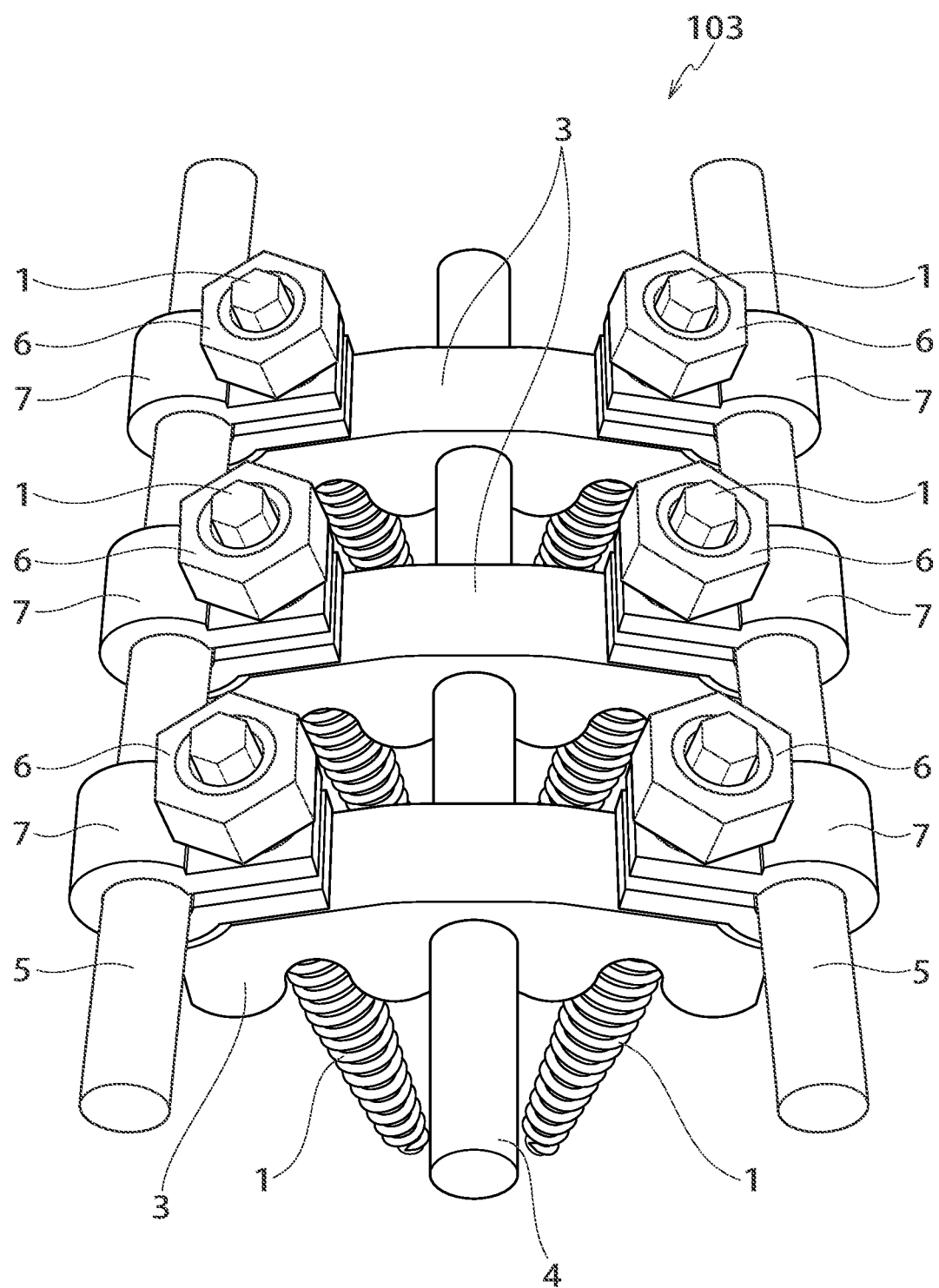
FIG. 9 is a photograph of a prototype of the spinal fusion implant shown in FIG. 8.

In the spinal fusion implant 103 which is a prototype and shown in FIG. 9, all of the screws 1, the connection plates 3, the center rod 4, the lateral rods 5, the nuts 6, and the pin members 7 are made of PEEK resin. In this connection, because an artifact appears around the spine fixed by a metal implant during MRI or CT photography, it is difficult to grasp the state of spinal neoplasm or a state of fusion of a grafted bone. When the components are made of a resin material or a carbon fiber material as in the spinal fusion implant 103 of the present embodiment, it is possible to prevent the occurrence of an artifact.

The inventors of the subject application performed an experiment of attaching a prototype spinal fusion implant 103 shown in FIG. 9 to the vertebrae of a pig. The inventors screwed (punctured) screws 1 into the vertebral bodies 51 along the guide holes 3c of the connection plates 3 while closely attaching the protrusions 8 (see FIG. 2) of each connection plate 3 to the concave portions of the intervertebral joints of the pig. As a result, the screws 1 were fixed to the vertebral bodies 51 without the occurrence of erroneous screwing (erroneous puncture). After the connection of the connection plates 3 by the center rod 4 and the lateral rods 5, the rotatability of the vertebral bodies were confirmed by a hand.

Figure 10:
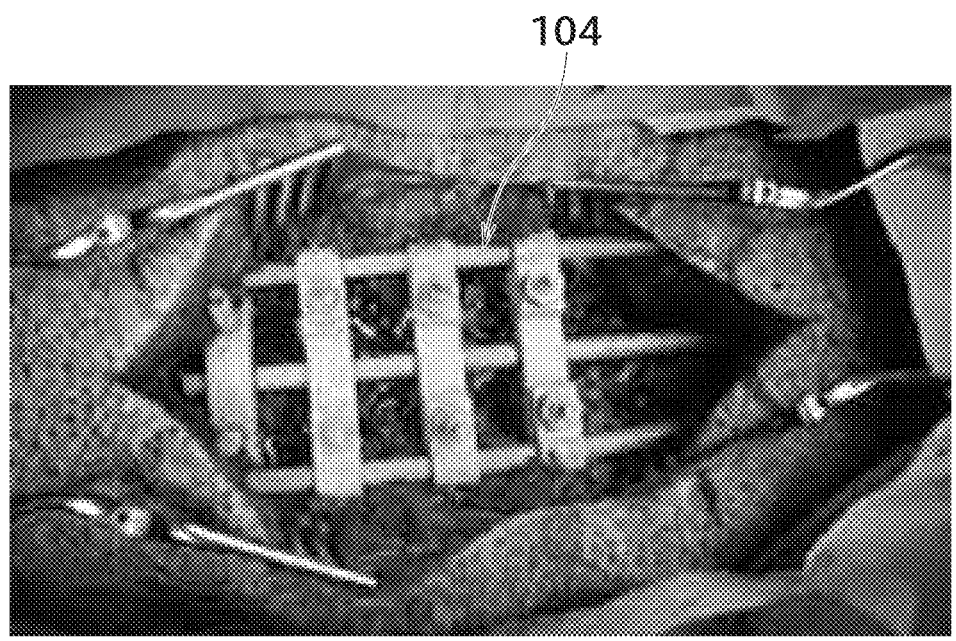
FIG. 10 is a photograph showing a state in which a spinal fusion implant made of PEEK resin has just been attached to the vertebrae of a pig with its back cut open.
Figure 11:
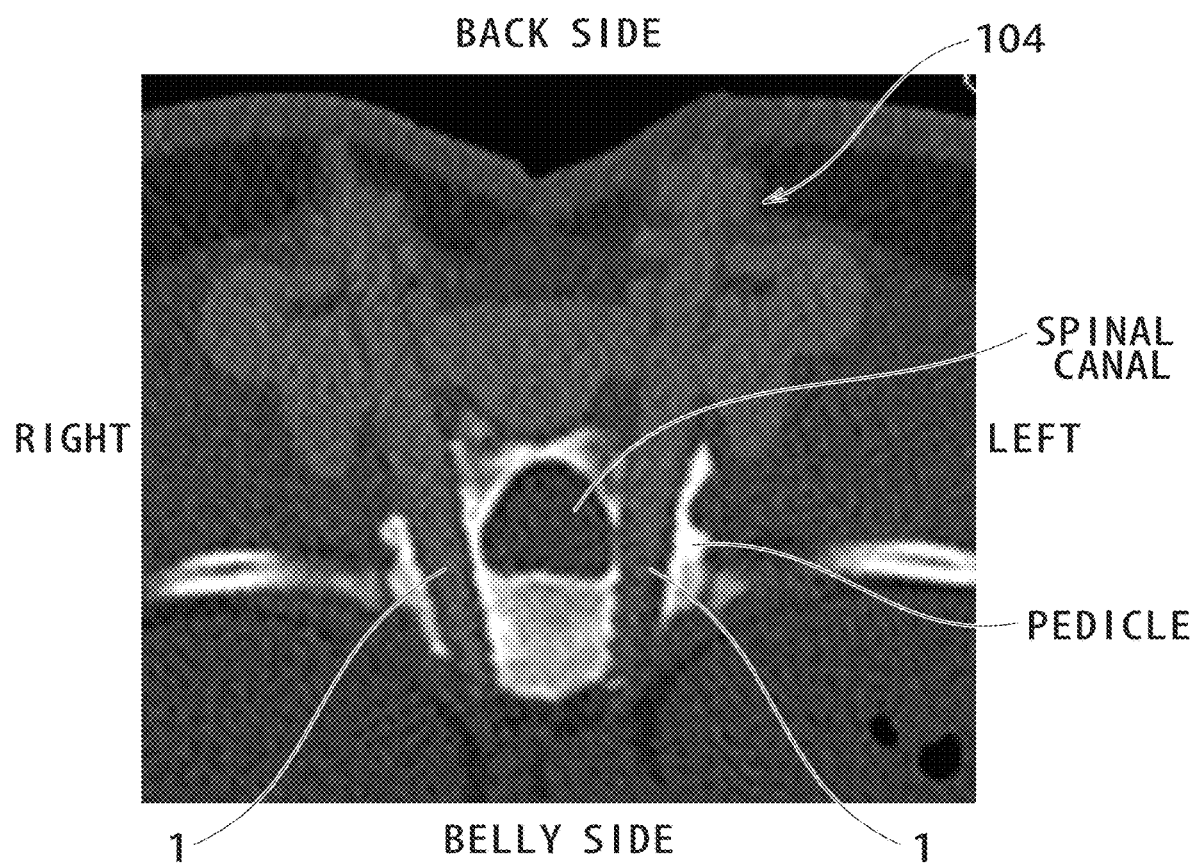
FIG. 11 is a CT image of the back portion of the pig in which the spinal fusion implant of FIG. 10 is embedded.
Figure 12:
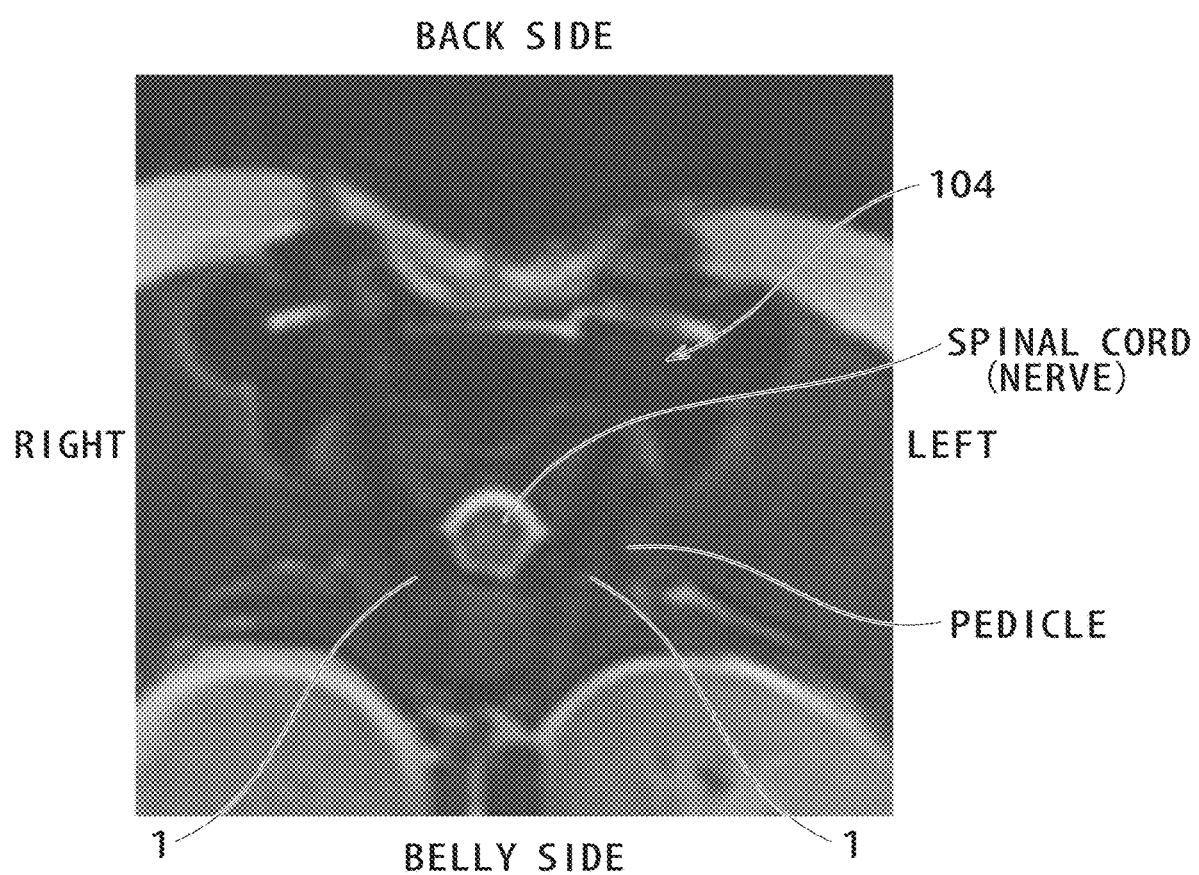
FIG. 12 is an MRI image of the back portion of the pig in which the spinal fusion implant of FIG. 10 is embedded.

FIG. 10 is a photograph showing a state in which a spinal fusion implant 104 made of PEEK resin has just been attached to the vertebrae of a pig with its back cut open. FIG. 11 and FIG. 12 are a CT image and an MRI image of the back portion of the pig in which the spinal fusion implant 104 is attached to the vertebrae (i.e., embedded in the body).

In the spinal fusion implant 104, three connection plates 3 are connected to one another by lateral rods 5 in addition to the center rod 4 and one connection plate 3 is connected only by the center rod 4. This spinal fusion implant 104 is different from the spinal fusion implant 102 shown in FIG. 7 in the number of connection plates 3 connected by the lateral rods 5.

As shown in FIG. 11 and FIG. 12, no artifact was observed in both the CT photography and the MRI photography because the spinal fusion implant 104 was made of a PEEK resin material. Furthermore, FIG. 11 and FIG. 12 show that the screws 1 are correctly punctured into the pedicles.

(Modifications)

While in the embodiment above three or four connection plates 3 are used, the number of the connection plates 3 is not limited to three or four. The number of the connection plates 3 may be two, or may be five or more.

While in the spinal fusion implants 102, 103, and 104 shown in FIG. 6 to FIG. 12 the lateral rods 5 are provided on the respective sides of the center rod 4, a lateral rod 5 may be provided on only one side of the center rod 4.

The embodiments of the present invention and their modifications have been described. It is a matter of course that other changes or alterations can be made on the present invention within the scope of envisagement of one skilled in the art.

REFERENCE SIGNS LIST

1: screw
3: connection plate
3a: back side surface
3b: belly side surface
3c: guide hole
3d: center hole
4: center rod
5: lateral rod
8: protrusion
50: vertebra
51: vertebral body
53: intervertebral joint
C: arc-shaped contour line of concave portion of intervertebral joint
D: imaginary circle
O: center of imaginary circle (rotation center)
L1: imaginary line
L2: imaginary curve
101, 102, 103, 104: spinal fusion implant

The invention claimed is:

1. A spinal fusion implant which keeps relative positions of neighboring vertebral bodies to fall within a predetermined range, comprising:
  screws configured to be connected to vertebral bodies;
  at least two connection plates in each of which guide holes, into which the screws are inserted from a back side surface toward a belly side surface, are formed at both end portions;
  a center rod which connects neighboring ones of the connection plates which are configured to be fixed to the vertebral bodies by the screws; and
  a lateral rod provided on either side of the center rod to connect neighboring ones of the connection plates,
  wherein each of the connection plates has, on the belly side surface, protrusions which are configured to be fitted into concave portions of intervertebral joints,
  wherein a center hole into which the center rod is slidably inserted is formed in side surfaces of each of the connection plates so that a center of the center hole is on a back side of an imaginary line which connects middle points of arc-shaped contour lines of the concave portions of the neighboring intervertebral joints when viewed from a head side of a human body,
  wherein the connection plates are rotatable about the center rod,
  wherein the lateral rod is attached to the connection plates by using pin members, and
  wherein each of the pin members includes:
    a ring-shaped rod holding portion into which the lateral rod is inserted; and
    a leg portion into which the screw is inserted, the leg portion making contact with the back side surface of each of the connection plates.

2. The spinal fusion implant according to claim 1, wherein,
  the center hole is positioned at a center of an imaginary circle which is assumed from the contour lines.

3. The spinal fusion implant according to claim 1, wherein,
  the center rod is curved based on data of a row of vertebrae in an upright position.

4. The spinal fusion implant according to claim 3, wherein,
  the center rod is curved along an imaginary curve which is formed by connecting centers of imaginary circles assumed from the contour lines, in a direction in which the vertebrae are lined up.

5. The spinal fusion implant according to claim 1, wherein,
  positions and angles of the guide holes in each of the connection plates are determined for each of the vertebral bodies so that the screws are accommodated inside the vertebral bodies.

6. The spinal fusion implant according to claim 1, wherein,
  the center rod is made of a resin material or a carbon fiber material.

7. The spinal fusion implant according to claim 1, wherein,
  the screws, the connection plates, and the center rod are made of a resin material or a carbon fiber material.

8. The spinal fusion implant according to claim 7, wherein the lateral rod is made of a resin material or a carbon fiber material.

9. The spinal fusion implant according to claim 1, wherein,
   a number of the connection plates is three or more and the connection plates are lined up in series, and
   at least two of the connection plates are connected with one another by the lateral rod.

10. The spinal fusion implant according to claim 1, wherein,
   a concave portion into which a part of the rod holding portion is fitted is formed at each of both ends of the back side surface of each of the connection plates.

\* \* \* \* \*